(12) United States Patent
Nakamura (10) Patent No.: US 8,693,753 B2
(45) Date of Patent: Apr. 8, 2014

(54) MEDICAL IMAGE PROCESSING DEVICE, METHOD AND PROGRAM

(71) Applicant: FUJIFILM Corporation, Tokyo (JP)

(72) Inventor: Keigo Nakamura, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 13/629,232

(22) Filed: Sep. 27, 2012

(65) Prior Publication Data

US 2013/0083982 A1    Apr. 4, 2013

(30) Foreign Application Priority Data

Sep. 30, 2011    (JP) ................................. 2011-217553

(51) Int. Cl.
G06K 9/00    (2006.01)
G06T 7/00    (2006.01)
G06F 19/00    (2011.01)

(52) U.S. Cl.
CPC ............ *G06T 7/0012* (2013.01); *G06F 19/321* (2013.01)
USPC ......................................................... 382/128

(58) Field of Classification Search
USPC ................................................. 382/128–134
See application file for complete search history.

(56) References Cited

U.S. PATENT DOCUMENTS 6,661,869 B2 * 12/2003 Menhardt ......................... 378/62
6,721,450 B2 * 4/2004 Tannenbaum et al. ......... 382/173
6,771,803 B1 * 8/2004 Turek et al. .................... 382/131
6,839,456 B2 * 1/2005 Touzawa et al. ............... 382/128
6,988,982 B2 * 1/2006 Melvin et al. .................... 600/16
7,079,674 B2 * 7/2006 Paragios et al. ................ 382/128
8,111,885 B2 * 2/2012 Von Berg et al. .............. 382/128
8,150,119 B2 * 4/2012 Zheng et al. ................... 382/128

FOREIGN PATENT DOCUMENTS

JP    2011-120825 A    6/2011

OTHER PUBLICATIONS

Si Yong Yeo et al. "A curvature-based approach for left ventricular shape analysis from cardiac magnetic resonance image" Med Bio Eng. Computer, 47:313-322. 2006.*
Qi Su, Kwan-Yee K. Wong, George S. K. Fung, "A Semi-Automatic Clustering-Based Level Set Method for Segmentation of Endocardium from MSCT Images", Department of Computer Science, U. of Hong Kong, NIH, 2007.*

(Continued)

*Primary Examiner* — Barry Drennan
*Assistant Examiner* — Oneal R Mistry
(74) *Attorney, Agent, or Firm* — McGinn IP Law Group, PLLC (57) ABSTRACT

A medical image processing device for extracting an endocardium of a left ventricle from 3D image data representing the left ventricle is provided. The device includes: a blood region extracting unit to extract a blood region in the left ventricle from the image data; a convex and concave points identifying unit to find a convex hull from sample points on a contour of the extracted blood region and identify convex points forming the convex hull and concave points, which are sample points other than the convex points; and an endocardium determining unit to deform the contour of the blood region by moving at least a part of the concave points outward from the blood region by an amount determined based on a positional relationship among each concave point and the convex points located around the concave point and determine a deformed contour of the blood region to be the endocardium.

14 Claims, 7 Drawing Sheets

(56) References Cited

OTHER PUBLICATIONS

Y. Zheng et al., "Four-Chamber Heart Modeling and Automatic Segmentation for 3D Cardiac CT Volumes Using Marginal Space Learning and Steerable Features", IEEE Transactions on Medical Imaging, vol. 27, No. 11, pp. 1668-1681, 2008.

* cited by examiner

MEDICAL IMAGE PROCESSING DEVICE, METHOD AND PROGRAM

BACKGROUND OF THE INVENTION

1. Field of the Invention

The present invention relates to a medical image processing device, a medical image processing method and a medical image processing program for extracting the endocardium of the left ventricle from 3D image data representing the left ventricle.

2. Description of the Related Art

Along with the spread of the multislice CT technology at medical treatment sites, medical image analyzing technologies are rapidly developing. For example, with respect to the heart region, it is now possible to obtain a plurality of 3D images during a single beat of the heart. With this development, functions of the heart, such as ejection rate, end-diastolic volume, end-systolic volume, single cardiac output, cardiac output and cardiac muscle weight, are analyzed by analyzing a plurality of pieces of 3D image data obtained by imaging the heart.

In order to achieve such analysis of the cardiac functions based on image information, it is necessary to accurately extract the position of the endocardium of the left ventricle from 3D image data representing the left ventricle. As a method for extracting the endocardium from the image data, a technique called Active Shape Model has been proposed, wherein a standard model of the endocardium of the left ventricle is deformed to conform to an image of interest in order to find the endocardium, as disclosed, for example, in Y. Zheng et al., "Four-Chamber Heart Modeling and Automatic Segmentation for 3D Cardiac CT Volumes Using Marginal Space Learning and Steerable Features", IEEE Transactions on Medical Imaging, Vol. 27, No. 11, pp. 1668-1681, 2008 (hereinafter, Non-patent Document 1).

In this technique, the standard model of the shape of the endocardium is generated in advance through learning the shape of the endocardium using a plurality of sample images. The standard model is represented by an average value and a principal component of the shape at each position. Then, the average shape of the generated standard model is placed on an image of interest, from which the shape of the endocardium is to be extracted. For each feature point on the average shape of the standard model placed on the image of interest, a feature quantity relative to a direction perpendicular to the shape is calculated and is compared with feature quantities which have been calculated during the learning, and an amount of shift, by which each feature point is to be moved to bring the feature point to a location where the best match is found between the feature quantities, is calculated. Then, a principal component factor which can best express the amount of shift calculated for each feature point is found, and the shape of the standard model is deformed using the thus found principal component factor. Further, for the deformed standard model, the calculation of the amount of shift and the deformation based on the result of the calculation are repeated until the shape is converged (until a predetermined energy function is minimized). Then, a finally obtained deformed standard model is obtained as the endocardium in the image of interest.

With the above-described conventional method, however, the shape of the endocardium to be extracted is limited by the standard model. Therefore, although the result of the extraction of the endocardium does not deviate from a proper shape of the endocardium, the endocardium in the image of interest may not accurately be extracted correspondingly to variation of the shape due to individual differences. For example, in a case where a convex portion or concave portion is locally present in the endocardium, some standard model cannot express such a shape of the endocardium in the image of interest, and even when an amount of shift for each feature point is correctly calculated, the shape may converge at a local solution (which is not an optimal solution), resulting in unsuccessful acquisition of a desired shape of the endocardium.

SUMMARY OF THE INVENTION

In view of the above-described circumstances, the present invention is directed to providing a medical image processing device, a medical image processing method and a medical image processing program which allow accurate detection of the endocardium of the left ventricle from 3D image data representing the left ventricle.

An aspect of the medical image processing device of the invention is a medical image processing device for extracting an endocardium of a left ventricle from 3D image data representing the left ventricle, the device including: a blood region extracting unit configured to extract a blood region in the left ventricle from the image data; a convex and concave points identifying unit configured to find a convex hull from a plurality of sample points on a contour of the extracted blood region and identify convex points forming the convex hull and concave points, which are sample points other than the convex points; and an endocardium determining unit configured to deform the contour of the blood region by moving at least a part of the concave points outward from the blood region by an amount determined based on a positional relationship among each concave point and the convex points located around the concave point and determine a deformed contour of the blood region to be the endocardium.

In the medical image processing device, the identification of the convex and concave points by the convex and concave points identifying unit and the deformation of the contour of the blood region by the endocardium determining unit may be carried out three-dimensionally on the 3D image data, or may be carried out two-dimensionally on pieces of 2D image data forming the 3D image data. At this time, the "points located around each concave point" refers to convex points located around each concave point for a three-dimensional process, or convex points located on both sides of each concave point for a two-dimensional process.

For example, in a case where the identification of the convex and concave points and the deformation of the contour are two-dimensionally carried out, the convex and concave points identifying unit may identify the convex points forming the convex hull and the concave points, which are the sample points other than the convex points, by finding the convex hull from the sample points on the contour of the extracted blood region in each of pieces of 2D image data representing cross sections perpendicular to an axis passing through the base and the apex of the heart set in the left ventricle; and the endocardium determining unit may obtain, in each of the pieces of 2D image data, a deformed contour of the blood region deformed by moving at least a part of the concave points outward from the blood region based on a positional relationship among each concave point and the convex points located on both sides of the concave point, and may determine the endocardium based on the deformed contour.

When the concave point to be moved is present within a predetermined range from the base of the heart in a direction of an axis passing through the base and the apex of the heart set in the left ventricle, the endocardium determining unit may make a degree of the movement of the concave point smaller than that in a case where the concave point to be moved is present outside the range.

Making the degree of the movement of the concave point smaller or larger refers to decreasing or increasing a value of a factor that multiplies an amount of movement of the concave point determined based on a positional relationship among the concave point of interest and the convex points located around the concave point of interest.

When the concave point to be moved is present within a predetermined range containing a central area between the base and the apex of the heart set in advance along the direction of the axis passing through the base and the apex of the heart set in the left ventricle, the endocardium determining unit may make the degree of the movement of the concave point larger than that in a case where the concave point to be moved is present outside the range. At this time, the degree of the movement (the factor) may not necessarily be constant within the range or outside the range, and may vary depending on the position along the direction of the set axis.

The endocardium determining unit may make the degree of the movement of the concave point smaller as an angle formed between straight lines respectively connecting an arbitrary point set in a central area between the blood region with convex points located around the concave point is larger.

The medical image processing device of the invention may further include an epicardium extracting unit configured to extract the epicardium of the left ventricle from the image data, wherein the endocardium determining unit may move at least the part of the concave points with setting an upper limit of the movement at a position at a predetermined distance inward from the extracted epicardium.

The medical image processing method of the invention is a method implemented by at least one computer executing the operations which are carried out by the individual units of the medical image processing device.

The medical image processing program of the invention is a program for causing at least one computer to carry out the above-described medical image processing method. This program is recorded on a recording medium, such as a CD-ROM or DVD, or in a storage of a server computer or a network storage in a downloadable state to be delivered to the user.

Figure 2:
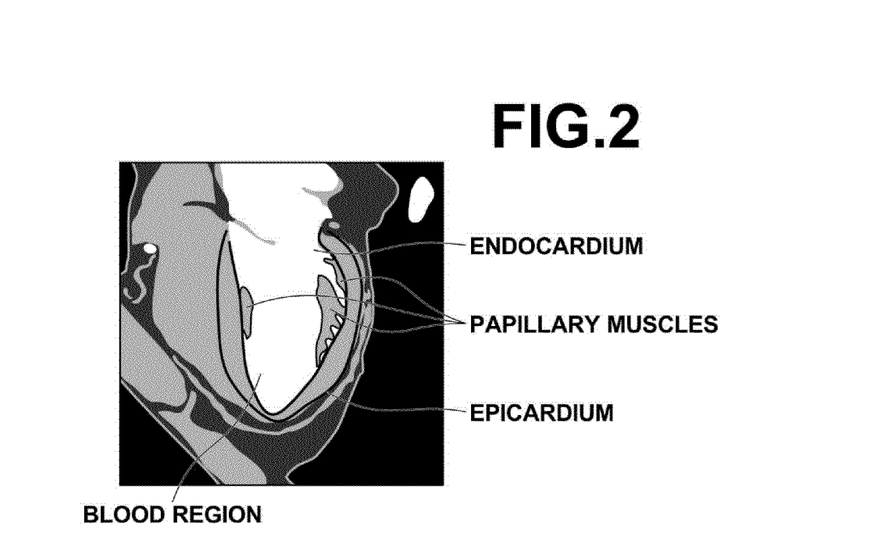
FIG. 2 is a diagram for explaining an outline of a process carried out according to the invention.

According to the medical image processing device, method and program of the invention, in order to extract the endocardium of the left ventricle from 3D image data representing the left ventricle, a blood region in the left ventricle is extracted from the image data. Then, a convex hull is found from sample points on a contour of the extracted blood region to identify convex points forming the convex hull and concave points, which are sample points other than the convex points. Then, the contour of the blood region is deformed by moving at least a part of the concave points outward from the blood region by an amount determined based on a positional relationship among each concave point and the convex points located around the concave point, and a deformed contour of the blood region is determined to be the endocardium. Therefore, as shown in FIG. 2, the deformed contour of the blood region, which is deformed to contain the papillary muscle regions located at the concave portion thereof, is determined to be the endocardium, thereby accurately extracting the endocardium of the left ventricle, which faces the blood region and the papillary muscles, correspondingly to variation of the shape due to individual differences. In this manner, the present invention can achieve more accurate extraction of the endocardium than that by the above-described conventional method, which extracts the endocardium by limiting the shape using a standard model.

DESCRIPTION OF THE PREFERRED EMBODIMENTS

Figure 1:
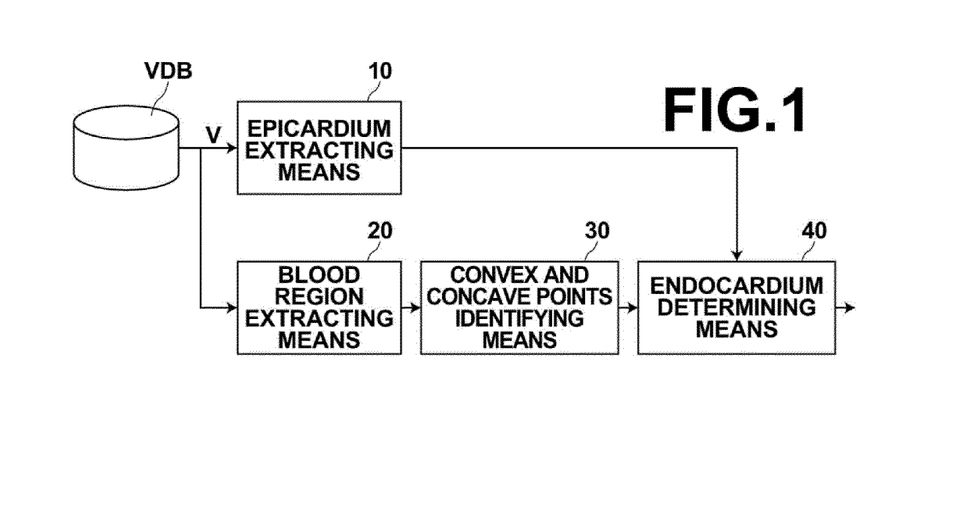
FIG. 1 is a diagram illustrating a schematic configuration of a medical image processing device according to an embodiment of the present invention.

Hereinafter, an embodiment of a medical image processing device, a medical image processing method and a medical image processing program of the present invention will be described in detail with reference to the drawings. FIG. 1 is a diagram illustrating a schematic configuration of a medical image processing device 1 according to an embodiment of the invention. The configuration of the medical image processing device 1 as shown in FIG. 1 is implemented by a computer executing a medical image processing program, which is read in an auxiliary storage device of the computer. The medical image processing program is distributed with being stored in a storage medium, such as a CD-ROM, or via a network, such as the Internet, to be installed on a computer. The medical image processing device 1 shown in FIG. 1 extracts the endocardium of the left ventricle from 3D image data representing the left ventricle. The medical image processing device 1 includes an epicardium extracting means 10, a blood region extracting means 20, a convex and concave points identifying means 30 and an endocardium determining means 40.

The epicardium extracting means 10 extracts the epicardium of the left ventricle from the 3D image data V representing the left ventricle. Specifically, the epicardium extracting means 10 positions and deforms a standard model of the shape of the left ventricle relative to the image data V so that the standard model is aligned with the left ventricle region in the image of interest in order to extract the epicardium (see Non-patent Document 1). The image data V is 3D image data of a subject formed by a group of 2D images, which are obtained by a Cr device, a MRI device, an ultrasound diagnostic device, or the like, for example, and is stored in a data storing means VDB.

The blood region extracting means 20 extracts a blood region in the left ventricle from the image data V. In this embodiment, the entire region inside the epicardium extracted by the epicardium extracting means 10 (which will hereinafter be referred to as "left ventricle region") is divided into the blood region and a cardiac muscle region including areas other than the blood region by a graph cuts method, and a boundary between the blood region and the surrounding region is determined to be a contour of the blood region.

Figure 3:
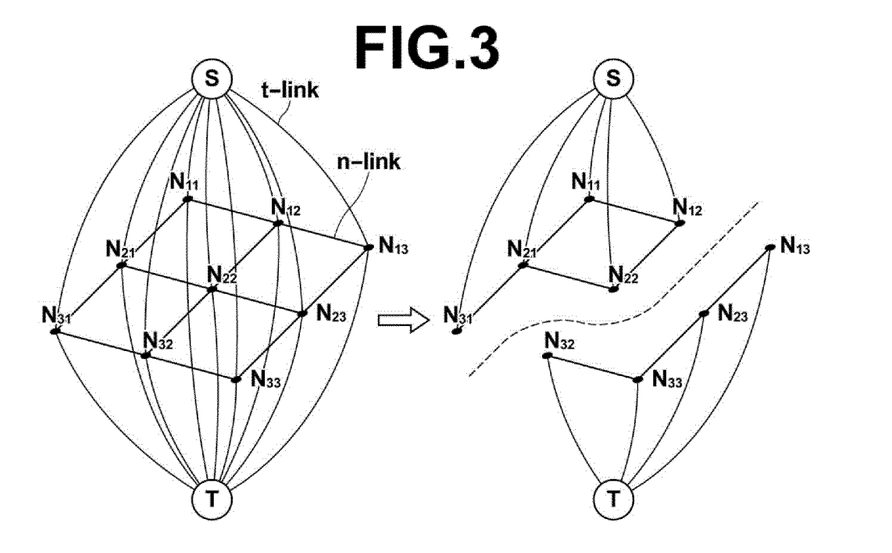
FIG. 3 is a diagram illustrating region segmentation by graph cuts.

Specifically, a graph including nodes $N_{ijk}$ representing voxels in the left ventricle region, nodes S and T representing labels (the blood region or the cardiac muscle region in this embodiment) which may be assigned to the voxels, n-links connecting the nodes of neighboring voxels, and t-links connecting the nodes $N_{ijk}$ representing voxels with the node S representing the blood region or the node T representing the cardiac muscle region is generated (see the right part of FIG. 3. It should be noted that FIG. 3 shows division of a two-dimensional region for ease of understanding).

Each n-link represents a probability of the neighboring voxels belonging to the same region. This probability can be found based on a difference between pixel values of the neighboring voxels. The t-link which connects the node $N_{ijk}$ representing each voxel with the node T representing the cardiac muscle region represents a probability of the voxel belonging to the cardiac muscle region. This probability can be calculated based on a result of determination as to whether or not the pixel value of the voxel is within a range (from about 30 to about 80) of a CT value of the cardiac muscle.

Figure 4:
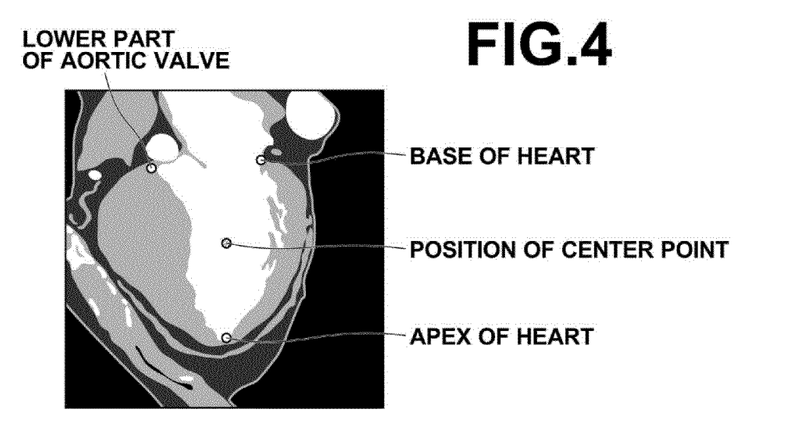
FIG. 4 is a diagram illustrating a position of a center point of the base of the heart, the apex of the heart and the lower part of the aortic valve.

The t-link which connects the node $N_{ijk}$ representing each voxel with the node S representing the blood region represents a probability of the voxel belonging to the blood region. This probability can be calculated based on statistical characteristics of pixel values of voxels in the neighborhood of the center point of three feature points which are obtained by detecting positions of the base of the heart (an upper portion of the heart connecting to the blood vessel), the apex of the heart (a pointing lower portion of the heart) and the lower part of the aortic valve from the image data V, as shown in FIG. 4, for example. The detection of the base of the heart, the apex of the heart and the lower part of the aortic valve may be achieved using classifiers, which are obtained by using a machine learning technique, such as AdaBoosting (see Japanese Unexamined Patent Publication No. 2011-120825).

Since the blood region and the cardiac muscle region are mutually exclusive regions, the region to be classified is divided into the blood region and the cardiac muscle region by cutting one of the two t-links connecting each node representing each pixel with the node S representing the blood region or the node T representing the cardiac muscle region, and cutting each n-link which connects the nodes of neighboring pixels having different labels (see the left part of FIG. 2). At this time, optimal region segmentation can be achieved by minimizing a sum of costs of all the t-links and n-links to be cut.

Figure 5:
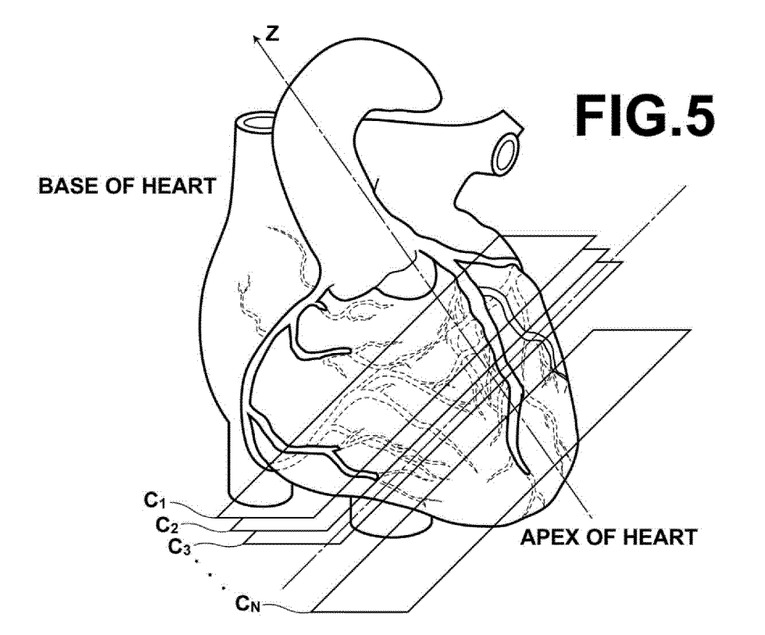
FIG. 5 is a diagram illustrating an axis and cross sections set in an operation to identify convex and concave points.

As shown in FIG. 5, the convex and concave points identifying means 30 sets an axis Z that passes through the base and the apex of the heart in the left ventricle region in the image data V, and finds a convex hull from a plurality of sample points on the contour of the extracted blood region in each of pieces of 2D image data C1 to CN, which represent cross sections perpendicular to the axis Z, to identify convex points forming the convex hull and concave points, which are sample points other than the convex points.

Figure 6:
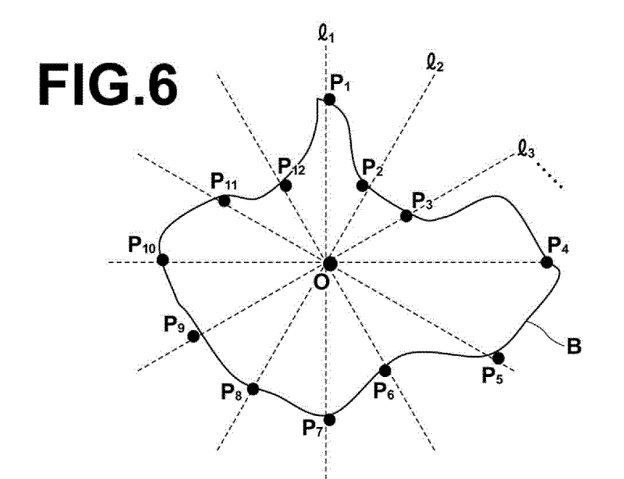
FIG. 6 is a diagram illustrating how sample points on a contour of a blood region are obtained.

Specifically, as shown in FIG. 6, first, in each piece of 2D image data Ci, line segments l1 to lm, which extend radially from a point of intersection O between the axis Z and the cross section (or a center point O set in the blood region) in different directions at equal angular intervals along the plane of the cross section, are set, and points P to Pm where the line segments li cross the contour B of the blood vessel region are obtained as the sample points. Although FIG. 6 shows an example where a total of 12 line segments are set at angular intervals of 30°, the angular intervals may be changed, such as setting 20 line segments at angular intervals of 18°.

Figure 7:
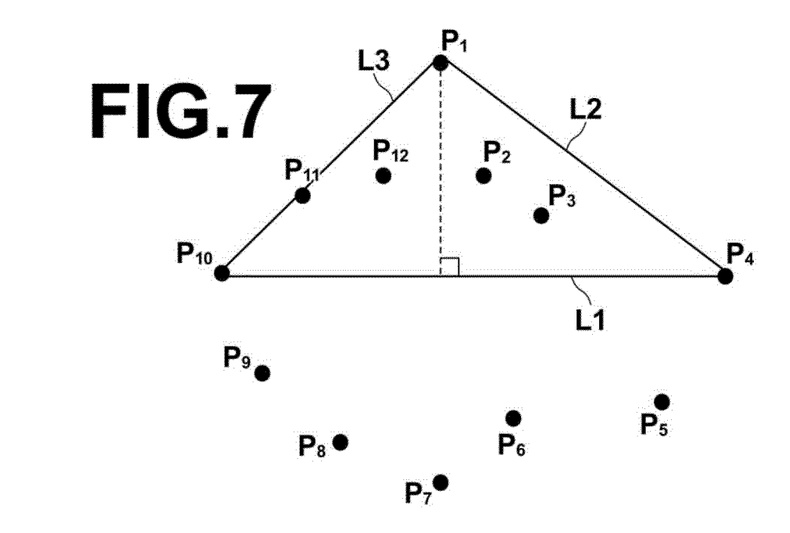
FIG. 7 is a diagram illustrating how a convex hull is obtained.

Then, the convex hull is found using the points P to Pm. The convex hull refers to a set of line segments which are formed by straight lines connecting outermost points in a given group of points. Now, how the convex hull is found is described. First, as shown in FIG. 7, two points P4 and P10 which have a maximum X coordinate and a minimum X coordinate are found from the points P to Pm, and a ridgeline L1 connecting these points is drawn. The thus drawn ridgeline L1 divides the region of interest into two regions above and below the ridgeline L1. Then, for each of these regions, a perpendicular line is drawn from each point toward the ridgeline and a point from which the longest perpendicular line is drawn is found. At this time, if no point with the longest perpendicular distance is found, the operation for the region of interest ends. In contrast, if the point is found, new ridgelines are added. FIG. 7 shows a state in which a point P1 with the longest perpendicular distance is found in the region above the ridgeline L1, and ridgelines L2 and L3 are added.

Figure 8:
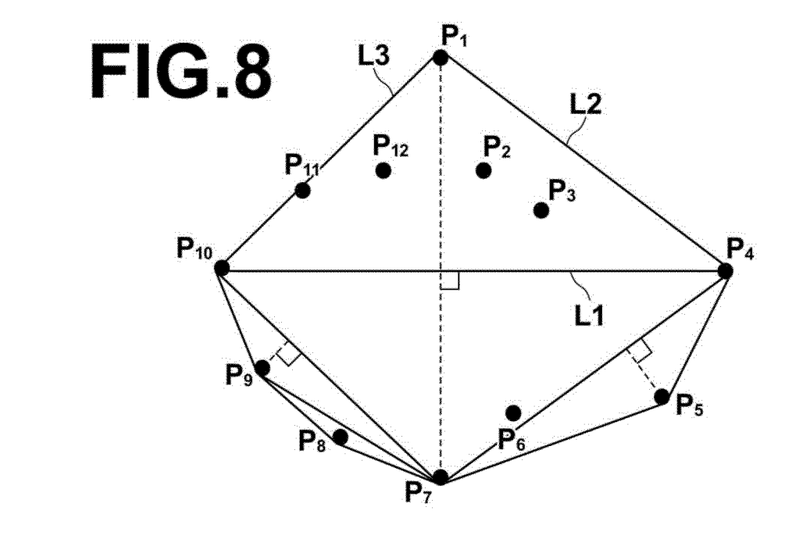
FIG. 8 is a diagram illustrating how the convex hull is obtained.
Figure 9:
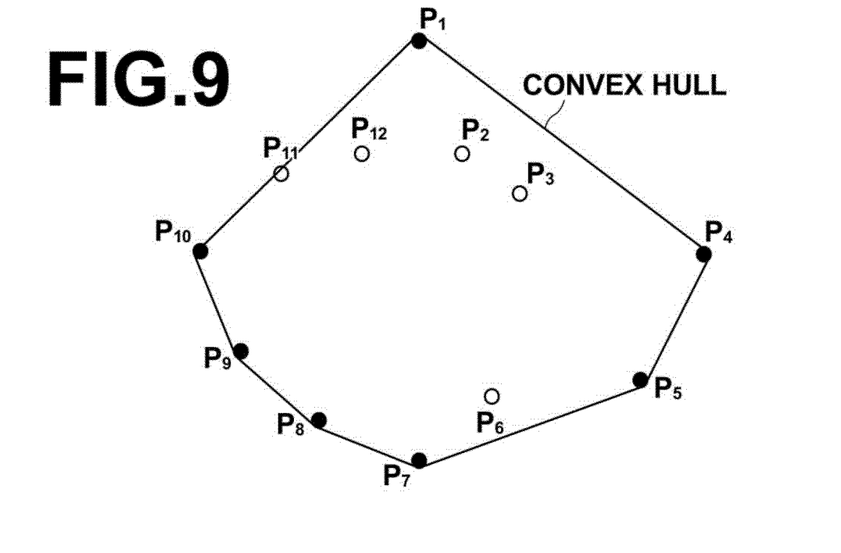
FIG. 9 is a diagram illustrating the convex hull, convex points and concave points obtained by the operation to identify convex and concave points.

When new ridgelines are added, the region of interest is further divided into two regions above and below the ridgelines. Then, the above-described operation to find a point from which the longest perpendicular line is drawn and to add new ridgelines is repeated until there is no point left outside the ridgelines, as shown in FIG. 8. In this manner, the convex hull is found and convex points P1, P4, P5 and P7 to P10 (indicated by filled circles in the drawing) forming the convex hull and concave points P2, P3, P6, P11 and P12 (indicated by open circles in the drawing), which are sample points other than the convex points, are identified, as shown in FIG. 9.

Figure 10:
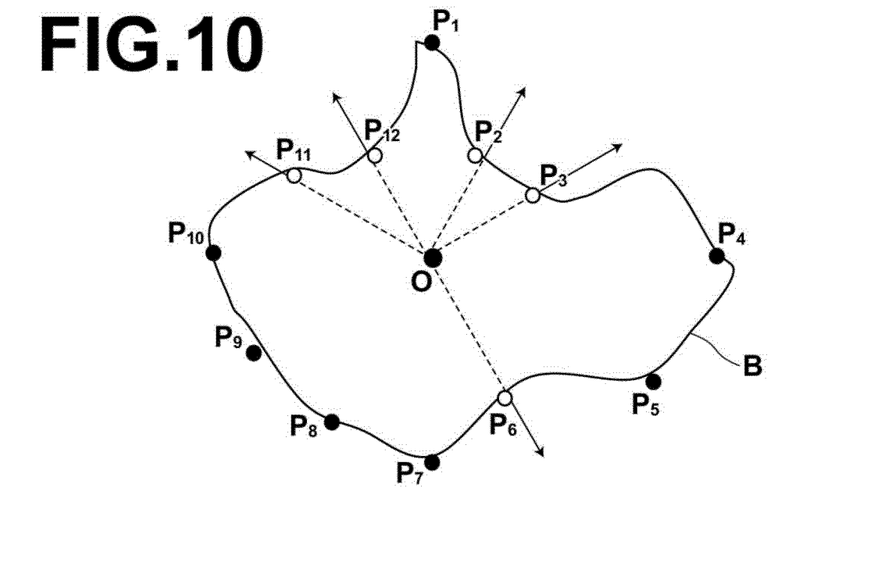
FIG. 10 is a diagram illustrating directions in which the concave points are moved in an operation to determine the endocardium.

As shown in FIG. 10, the endocardium determining means 40 moves each of the concave points P2, P3, P6, P11 and P12 identified by the above-described process outward from the contour B of the blood region by an amount determined based on a positional relationship among the concave point and two convex points located on both sides of the concave point to deform the contour B of the blood region, and determines a deformed contour B' to be the endocardium. At this time, each concave point is moved radially from the point of intersection O (or the center point O set in the blood region), and the amount of movement is determined based on the position of the concave point of interest (concave point to be moved) relative to the point of intersection O and distances from the point of intersection O to the convex points located on both sides of the concave point of interest.

Figure 11:
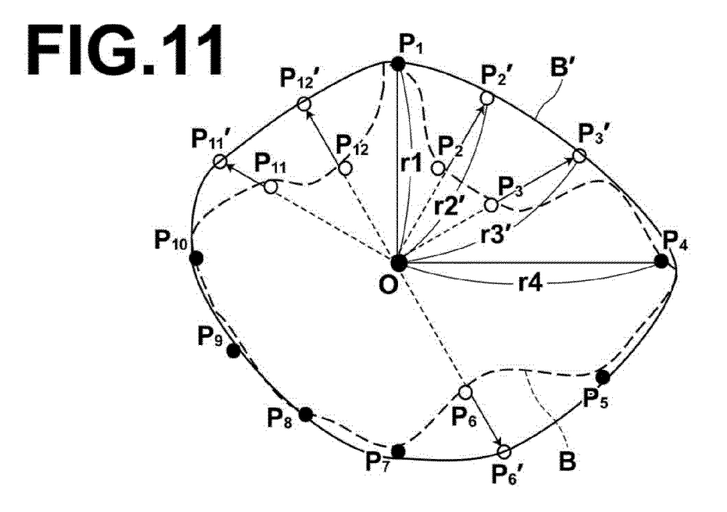
FIG. 11 is a diagram for explaining how an amount of movement for each concave point is calculated.

For example, as shown in FIG. 11, the concave point P2 is moved radially from the point of intersection O such that a distance r2' from the point of intersection O to the moved concave point P2' is a value calculated according to Equation (1) below, and the concave point P3 is moved radially from the point of intersection O such that a distance r3' from the point of intersection O to a moved concave point P3' is a value calculated according to Equation (2) below:

$$r2' = W1 \times W2 \times W3 \times (2 \times r1 + 1 \times r4)/3 \qquad (1) \text{ and}$$

$$r3' = W1 \times W2 \times W3 \times (1 \times r1 + 2 \times 0r4)/3 \qquad (2),$$

where r1 is a distance from the point of intersection O to the convex point P1, r4 is a distance from the point of intersection O to the convex point P4, and W1, W2 and W3 are factors which are defined as described below.

In Equations (1) and (2) above, the value of the factor W1 is set based on a position of the concave point of interest along the direction of the axis Z passing through the base and the apex of the heart set in the left ventricle. Specifically, if the concave point of interest is present within a predetermined range from the base of the heart along the direction of the axis Z, the factor W1 has a value smaller than that when the concave point of interest is present outside the range, and if the concave point of interest is present within a predetermined range, which is set in advance to contain a central area between the base and the apex of the heart, along the direction of the axis Z, the factor W1 has a value larger than that when the concave point of interest is present outside the range.

For example, if the concave point of interest is present within a range of 10 mm from the base of the heart along the direction of the axis Z, W1=0.0, and if the concave point of interest is present outside the range of 10 mm from the base of the heart, W1=max (0.5, 1.0−a distance from a reference point T/20 mm). The reference point T is a point on the axis Z. The reference point T is set in advance at a position along the direction of the axis Z where the largest number of papillary muscles are present, and is at a position defined by a midpoint between the base and the apex of the heart, or: 0.4×the position of the base of the heart+0.6×the position of the apex of the heart. Thus, in the 2D image data within a certain range (10 mm, for example) from the base of the heart, the contour of the blood region is not deformed. In the 2D image data outside the range, the degree of deformation to extend the contour of the blood region is smaller as the distance between the concave point of interest and the reference point T is larger.

Figure 12:
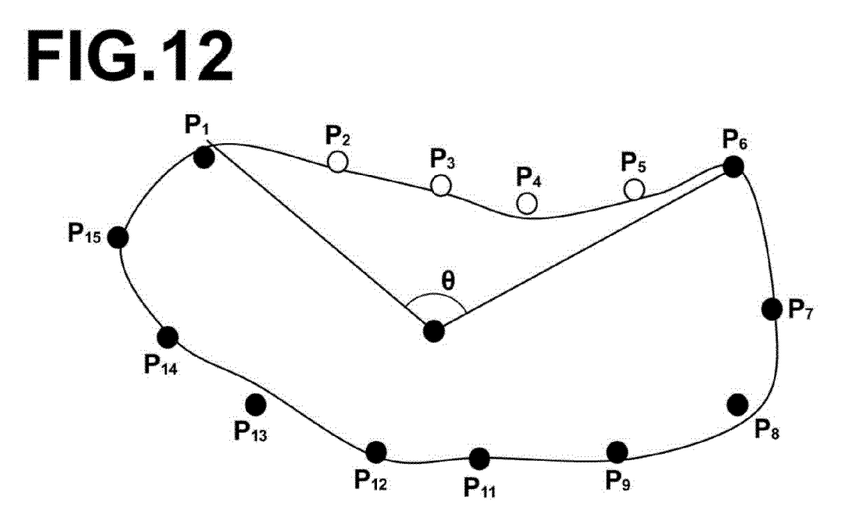
FIG. 12 is a diagram for explaining how a factor W2 is set.

In the above Equations (1) and (2), the value of the factor W2 is set such that the factor W2 is smaller as an angle formed between two straight lines connecting the point of intersection O with two convex points located on both sides of the concave point of interest, respectively, is larger. For example, as shown in FIG. 12, an angle θ formed between two straight lines connecting the point of intersection O with two convex points P1 and P6 located on both sides of the concave point of interest, respectively, is smaller than 100°, the factor W2=1.0−θ/100 for the concave points P2 to P5 located between the convex points P1 and P6. If the angle θ is equal to or larger than 100°, the factor W2=0.0. Thus, the degree of deformation to extend the contour of the blood region is smaller as the spread of the concave shape of the blood region is larger, and when the angle of the spread is more than 100°, the contour of the blood region is not deformed.

Figure 13:
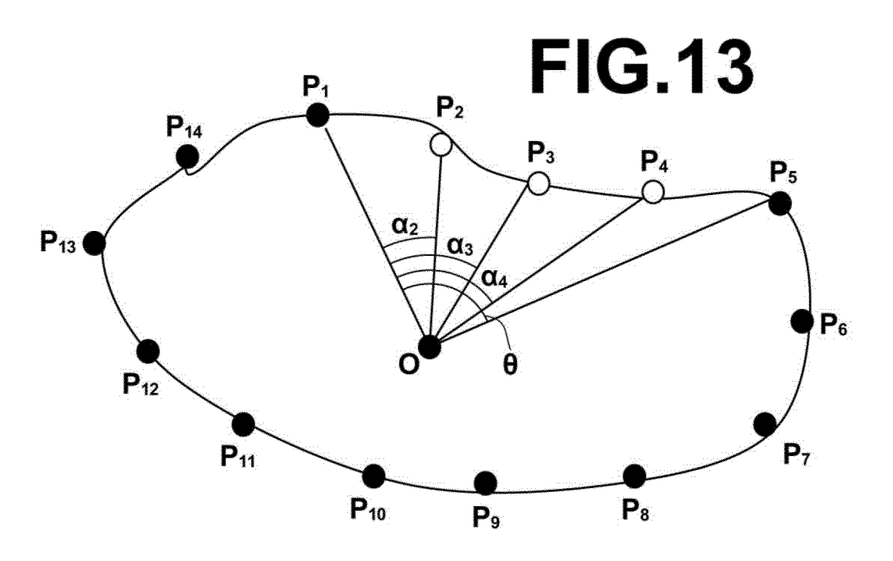
FIG. 13 is a diagram for explaining how a factor W3 is set.

In the above Equations (1) and (2), the value of the factor W3 is set to be smaller as the position of the concave point of interest is nearer to the center position of the concave shape in which the concave point is located. For example, as shown in FIG. 13, when an angle θ is formed between two straight lines connecting the point of intersection O with two convex points located on both sides of the concave point of interest, respectively, and an angle αi (i=2, 3, 4) is formed between a straight line connecting the point of intersection O with the concave point of interest and a straight line connecting the point of intersection O with a convex point located on one side of the concave point of interest, W3=0.8+0.2×(|αi−θ/2|)/(θ/2).

Further, when the endocardium determining means 40 moves each concave point of interest radially from the point of intersection O by the amount of movement determined as described above, the upper limit of the movement may be set at a position at a predetermined distance inward from the epicardium extracted by the epicardium extracting means 10 so that the concave point is not moved beyond the upper limit, thereby preventing over-extraction of the blood region.

As described above, according to the medical image processing device, method and program of this embodiment, when the endocardium of the left ventricle is extracted from the 3D image data V representing the left ventricle, the blood region extracting means 20 extracts the blood region in the left ventricle from the image data V, the convex and concave points identifying means 30 finds a convex hull from the sample points P to Pm on the extracted contour B of the blood region to identify the convex points forming the convex hull and concave points, which are sample points other than the convex points, and the endocardium determining means 40 deforms the contour B of the blood region by moving at least a part of the concave points outward from the blood region by an amount determined based on a positional relationship among each concave point and convex points located around the concave point and determines the deformed contour B' of the blood region to be the endocardium. Therefore, the endocardium of the left ventricle facing the blood region and the papillary muscles can be accurately extracted correspondingly to variation of the shape due to individual differences. In this manner, the present invention can achieve more accurate extraction of the endocardium than that by the above-described conventional method, which extracts the endocardium by limiting the shape using a standard model.

Although the blood region extracting means 20 extracts the blood region using the graph cuts method in the above-described embodiment, the blood region extracting means 20 may extract the blood region using a region segmentation method other than the graph cuts method. For example, the blood region may be found using a region growing method, which achieves division of a region by founding a center point of three feature points including the base of the heart, the apex of the heart and the lower part of the aortic valve, and integrating neighboring voxels having the same or similar pixel values as that of the voxel at the center point to grow a region. At this time, a range of a CT value of the blood region, which is obtained from pixel values of voxels located in the neighborhood of the center point, may be used as a condition for the region growing.

Although the convex and concave points identifying means 30 uses all the sample points other than the convex points forming the convex hull as control points (concave points to be moved) to deform the blood region in the above-described embodiment, the convex and concave points identifying means 30 may identify a concave shape portion in the contour of the blood region by finding a convex hull, and may newly set control points for deforming the blood region from points located on the concave shape on the contour to deform and extend the blood region using the set control points.

The convex and concave points identifying means 30 may determine the convex hull region found by using the sample points to be the endocardium, or may determine an OR region of the convex hull region, which is found by using the endocardium determined in the above-described embodiment and the sample points, to be the final endocardium.

Although the endocardium determining means 40 uses, as the final amount of movement of each concave point, a value obtained by multiplying the amount of movement of the concave point, which is determined based on a positional relationship among the concave point of interest and the convex points located around the concave point of interest, with the factors W1, W2 and W3 in the above-described embodiment, the endocardium determining means 40 may use, as the final amount of movement of the concave point, the amount of movement of each concave point determined based on a positional relationship among the concave point of interest and the convex points located around the concave point of interest, or a value obtained by multiplying the amount of movement with one or two factors selected from the factors W1, W2 and W3.

What is claimed is:

1. A medical image processing device for extracting an endocardium of a left ventricle from 3D image data representing the left ventricle, the device comprising:
    a blood region extracting unit configured to extract a blood region in the left ventricle from the image data;
    a convex and concave points identifying unit configured to find a convex hull from a plurality of sample points on a contour of the extracted blood region and identify convex points forming the convex hull and concave points, which are sample points other than the convex points; and
    an endocardium determining unit configured to deform the contour of the blood region by moving at least a part of the concave points outward from the blood region by an amount determined based on a positional relationship among each concave point and the convex points located around the concave point and determine a deformed contour of the blood region to be the endocardium.

2. The medical image processing device as claimed in claim 1, wherein
    the convex and concave points identifying unit identifies the convex points forming the convex hull and the concave points, which are the sample points other than the convex points, by finding the convex hull from the sample points on the contour of the extracted blood region in each of pieces of 2D image data representing cross sections perpendicular to an axis passing through a base and an apex of a heart set in the left ventricle; and
    the endocardium determining unit obtains, in each of the pieces of 2D image data, a deformed contour of the blood region deformed by moving at least a part of the concave points outward from the blood region based on a positional relationship among each concave point and the convex points located on both sides of the concave point, and determines the endocardium based on the deformed contour.

3. The medical image processing device as claimed in claim 1, wherein, when the concave point to be moved is present within a predetermined range from a base of a heart along a direction of an axis passing through the base and an apex of the heart set in the left ventricle, the endocardium determining unit makes a degree of the movement of the concave point smaller than that in a case where the concave point to be moved is present outside the range.

4. The medical image processing device as claimed in claim 1, wherein, when the concave point to be moved is present within a predetermined range containing a central area between a base and an apex of a heart set in advance along a direction of an axis passing through the base and the apex of the heart set in the left ventricle, the endocardium determining unit makes a degree of the movement of the concave point larger than that in a case where the concave point to be moved is present outside the range.

5. The medical image processing device as claimed in claim 1, wherein the endocardium determining unit makes a degree of the movement of the concave point smaller as an angle formed between straight lines respectively connecting an arbitrary point set in a central area between the blood region with convex points located around the concave point is larger.

6. The medical image processing device as claimed in claim 1, further comprising an epicardium extracting unit configured to extract an epicardium of the left ventricle from the image data,
    wherein the endocardium determining unit moves at least the part of the concave points with setting an upper limit of the movement at a position at a predetermined distance inward from the extracted epicardium.

7. A medical image processing method for extracting an endocardium of a left ventricle from 3D image data representing the left ventricle, the method comprising the steps of:
    extracting a blood region in the left ventricle from the image data;
    finding a convex hull from a plurality of sample points on a contour of the extracted blood region and identifying convex points forming the convex hull and concave points, which are sample points other than the convex points; and
    deforming the contour of the blood region by moving at least a part of the concave points outward from the blood region by an amount determined based on a positional relationship among each concave point and the convex points located around the concave point and determining a deformed contour of the blood region to be the endocardium.

8. The medical image processing method as claimed in claim 7, wherein the step of identifying the convex and concave points comprises identifying the convex points forming the convex hull and the concave points, which are the sample points other than the convex points, by finding the convex hull from the sample points on the contour of the extracted blood region in each of pieces of 2D image data representing cross sections perpendicular to an axis passing through a base and an apex of a heart set in the left ventricle; and
    the step of determining the endocardium comprises obtaining, in each of the pieces of 2D image data, a deformed contour of the blood region deformed by moving at least a part of the concave points outward from the blood region based on a positional relationship among each concave point and the convex points located on both sides of the concave point, and determining the endocardium based on the deformed contour.

9. The medical image processing method as claimed in claim 7, wherein the step of determining the endocardium comprises, when the concave point to be moved is present within a predetermined range from a base of a heart along a direction of an axis passing through the base and an apex of the heart set in the left ventricle, making a degree of the movement of the concave point smaller than that in a case where the concave point to be moved is present outside the range.

10. The medical image processing method as claimed in claim 7, wherein the step of determining the endocardium comprises, when the concave point to be moved is present within a predetermined range containing a central area between a base and an apex of a heart set in advance along a direction of an axis passing through the base and the apex of the heart set in the left ventricle, making a degree of the movement of the concave point larger than that in a case where the concave point to be moved is present outside the range.

11. The medical image processing method as claimed in claim 7, wherein the step of determining the endocardium comprises making a degree of the movement of the concave point smaller as an angle formed between straight lines respectively connecting an arbitrary point set in a central area between the blood region with convex points located around the concave point is larger.

12. The medical image processing method as claimed in claim 7, further comprising extracting an epicardium of the left ventricle from the image data,
    wherein the step of determining the endocardium comprises moving at least the part of the concave points with setting an upper limit of the movement at a position at a predetermined distance inward from the extracted epicardium.

13. A non-transitory computer readable medium containing a medical image processing program for causing a computer to execute an operation to extract an endocardium of a left ventricle from 3D image data representing the left ventricle, the program causing the computer to carry out the steps of:
    extracting a blood region in the left ventricle from the image data;
    finding a convex hull from a plurality of sample points on a contour of the extracted blood region and identifying convex points forming the convex hull and concave points, which are sample points other than the convex points; and
    deforming the contour of the blood region by moving at least a part of the concave points outward from the blood region by an amount determined based on a positional relationship among each concave point and the convex points located around the concave point and determining a deformed contour of the blood region to be the endocardium.

14. The non-transitory computer readable medium as claimed in claim 13, wherein the step of identifying the convex and concave points comprises identifying the convex points forming the convex hull and the concave points, which are the sample points other than the convex points, by finding the convex hull from the sample points on the contour of the extracted blood region in each of pieces of 2D image data representing cross sections perpendicular to an axis passing through a base and an apex of a heart set in the left ventricle; and
    the step of determining the endocardium comprises obtaining, in each of the pieces of 2D image data, a deformed contour of the blood region deformed by moving at least a part of the concave points outward from the blood region based on a positional relationship among each concave point and the convex points located on both sides of the concave point, and determining the endocardium based on the deformed contour.

* * * * *